United States Patent [19]

Ham et al.

[11] Patent Number: 5,729,582

[45] Date of Patent: Mar. 17, 1998

[54] METHOD AND APPARATUS FOR DETERMINING BOTH DENSITY AND ATOMIC NUMBER OF A MATERIAL COMPOSITION USING COMPTON SCATTERING

[76] Inventors: Young S. Ham, Safeguards Division TCNC. , Korea Atomic Energy Research Institute, Taejum, Rep. of Korea; Chester F. Poranski, Gainer St., Annandale, Va. 22003

[21] Appl. No.: 656,528

[22] Filed: May 31, 1996

[51] Int. Cl.[6] ................................................ G01N 23/201
[52] U.S. Cl. ............................... 378/89; 378/86; 378/88
[58] Field of Search ................................. 378/86, 87, 88, 378/89

[56] References Cited

U.S. PATENT DOCUMENTS

| | | | |
|---|---|---|---|
| 4,029,963 | 6/1977 | Alvarez et al. | 378/5 |
| 4,768,214 | 8/1988 | Bjorkholm | 378/87 |
| 5,420,905 | 5/1995 | Bertozzi | 378/88 |

*Primary Examiner*—David P. Porta
*Assistant Examiner*—David Vernon Bruce

[57] ABSTRACT

An x-ray backscatter tomography system includes a collimated x-ray source for directing a collimated beam towards a target at a select position and orientation, a first detector array for measuring photons scattered at a selected first angle, and a second detector array for measuring photons scattered at a selected second angle different from the first angle. The system is also responsive to the first and second detectors for calculating the density and atomic number of the target.

18 Claims, 1 Drawing Sheet

METHOD AND APPARATUS FOR DETERMINING BOTH DENSITY AND ATOMIC NUMBER OF A MATERIAL COMPOSITION USING COMPTON SCATTERING

BACKGROUND OF THE INVENTION

1. Field of the Invention

The purpose of this invention is to obtain the spatial distribution of the material properties of an object in terms of both density and atomic number, nondestructively, using Compton scattering.

2. Description of the Related Art

Radiant energy systems have been used before to determine the density of the material of an object.

Compton scattering is the dominant interaction in the range of x-ray energies commonly used in industrial radiography. It occurs when interaction between an incident x-ray photon and a free or outer shell electron causes the electron to recoil and a scattered photon to be propagated in a new direction with a reduced energy. As the incident x-ray photon energy increases, the mean scatter direction moves toward the incident beam direction. Even at relatively high energies, some photons are scattered in the backwards direction.

A distinct angle is formed between the incident and scattered photon. This angle represents the difference in energy of the incident and scattered rays. Accordingly, this difference in energy of the incident and scattered rays is directly related to the angle formed between their respective ray paths.

The direction and reduced energy of the Compton scattered photons can be expressed from the known principle of the conservation of momentum. The known expression for the energy of the scattered photon in terms Of the photon scattering angle $\theta$ is $$E'(E_0, \theta) = \frac{E_0}{1 + \frac{E_0}{m_0 c^2}(1 - \cos\theta)} \quad (1)$$

where $E_0$ is the energy of the incident photon, E' is the energy of the scattered photon at a particular angle, and $m_0 c^2$ is the rest mass energy of an electron (511 KeV).

The probability of Compton scattering in a unit volume is expressed as a product of electron density, $\rho_e$, and Compton cross section per electron, $\sigma_{c_1}^e$.

The electron density is defined as $$\rho_e = \rho \frac{N_A Z}{W} \quad (2)$$

where $\rho$ is the physical density in g/cm3, $N_A$ is Avogadro's number, Z is atomic number, and W is atomic weight. Since Z/W is nearly constant for low Z materials with the exception of hydrogen, electron density is proportional to the physical density of a sample. Thus by counting the single Compton scattered photons, one can estimate the density of an unknown material, assuming the attenuations due to the material between the source, scattering point and detector are negligible.

Using these properties, there have been numerous attempts to investigate the inner structures of materials. Medical applications have been demonstrated using the backscatter signal to measure tissue densities (P. G. Lale, "The Examination of Internal Tissues, Using Gamma-Ray Scatter with a Possible Extension of Megavoltage Radiography", *Physics in Medicine and Biology*, Vol. 4, 1959; R. L. Clarke and G. Van Dyk, "A New Method for Measurement of Bone Mineral Content Using Both Transmitting and Scattered Beams of Gamma-rays", *Physics in Medicine and Biology*, Vol. 18, No. 4, pp. 532-539, 1973). Research has also been reported on a variety of industrial backscatter imaging techniques and applications (H. Berger, Y. T. Cheng, and E. L. Criscuolo, "High Sensitivity, One Sided X-ray Inspection System", *NSWC TR-85-292*, Jul. 1985; D. G. Costello, J. A. Stokes, and A. P. Trippe, "Theory and Applications of Collimated Photon Scattering", 14th *Symposium on Nondestructive Evaluation*, San Antonio, Tex., 1983; Y. S. Ham, E. C. Greenawald, and C. F. Poranski, "X-ray Backscatter Inspection of Low Density, Low Atomic Number Materials", *Proceedings in Radiologic NDT III: Advancements, Automation, and Imaging*, Atlantic City, N.J., 1993; H. Strecker, "Scatter Imaging of Aluminum Castings Using an X-ray Fan Beam and a Pinhole Camera", *Materials Evaluation*, Vol. 40, 1982). Both in medical or industrial applications, electron densities of the sample have been obtained for densitometric purposes. Current X-ray backscatter systems solely image the densities of homogenous low atomic number materials, thus limiting their applicability.

However, systems or methods used thus far have not determined both density and atomic number of the material of an object.

SUMMARY OF THE INVENTION

It is therefore an object of the present invention to provide a method and apparatus for determining both density and atomic number of the material of an object, using a novel design and the property that the energy of a Compton scattered photon is a function of the scatter angle.

In the present invention, x-ray backscatter tomography (XBT) is utilized, which requires access to only one side of an object for nondestructive inspection. For light materials inspection, it can provide detection of delamination, foreign inclusion, porosities, moisture and air bubbles by mapping the volumetric density distribution. Furthermore, the method is especially valuable for inspecting light materials inside a heavy object when high energy photons are used.

Accordingly, the present invention provides a unique and potentially enormously useful tool for imaging of internal structures from only one side. Also, the novel XBT system of the present invention can map images in terms of both density and the atomic number, while current systems can only provide the density distribution.

It is another object of the present invention to obtain the three dimensional information about the overlaying material by scanning an object from the surface to deeper layers in a raster fashion. Thus, complete information about the object can be obtained with the removal of the serious attenuation artifacts present in the current systems. Such systems extend XBT inspection to higher atomic number materials even with inhomogeneity. This additional feature opens "a new chapter" for one-sided inspection applicability. XBT is no longer limited to the inspection of homogeneous, or low density materials.

By using XBT according to the present invention, one can characterize corrosion, fractures or other flaws in a variety of materials, for example, in complex, layered metallic and combination metallic, composite and honeycomb structures found in airplanes. One can also inspect any defects in a material, for example, defects underneath the surface of space shuttle tiles or any broken cords in steel-reinforced sonar domes on ships. Although the aforementioned applications have been described, the present invention is not limited to these applications.

DETAILED DESCRIPTION OF THE PREFERRED EMBODIMENTS

Figure 1:
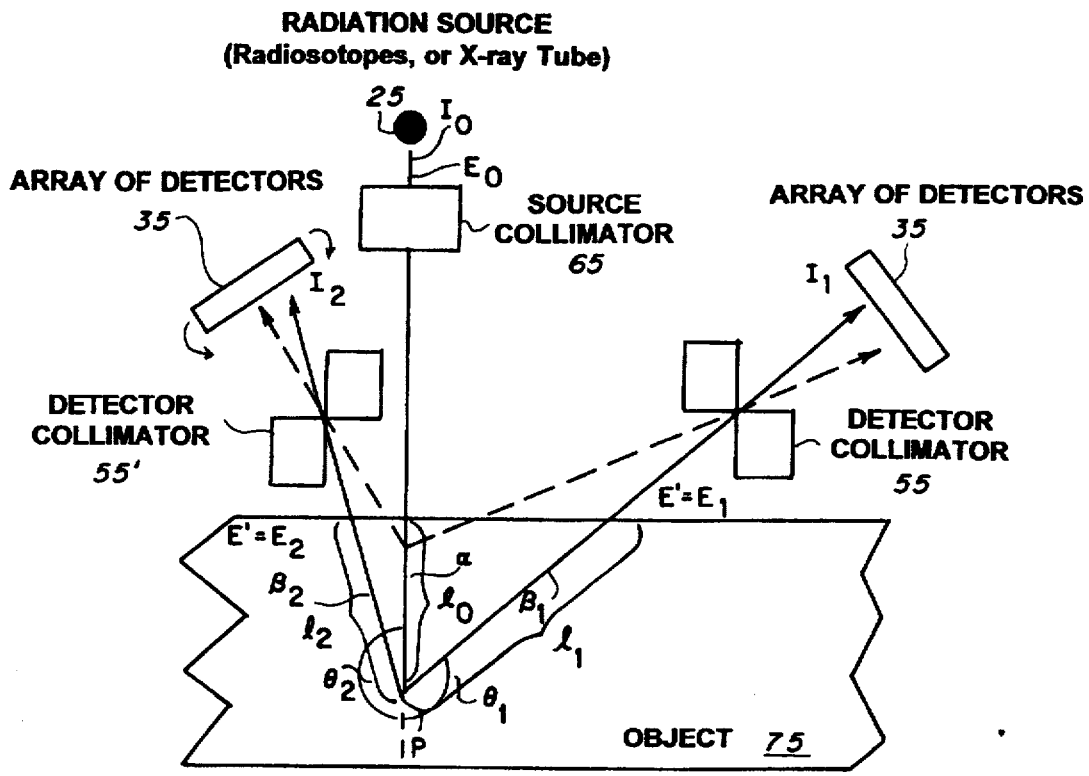
FIG. 1 illustrates an x-ray backscatter tomography (XBT) system according to a preferred embodiment of the present invention.

The x-ray backscatter tomography (XBT) system of a preferred embodiment of the present invention is shown in FIG. 1. The system consists of a collimated x-ray source producing a narrow vertical, pencil beam and two arrays of collimated detectors, each array forming a single detector collimator. Each single detector collimator with its set of multiple collimated detectors is used such that many depths are measured by each detector collimator simultaneously. A rectangular slit with a desired size can be used rather than a pin-hole to increase the photon flux at the detector surfaces. The arrays of detectors can be slanted as shown or they could be parallel to the object surface. The advantage of parallel arrays is that the photons that are scattered at a deeper layer have a shorter path length to the detector, which increases the photon counts.

In FIG. 1, a point of intersection, P, (the volume element of the object of interest) is scanned simultaneously at two different scattered energies, $E_1$, and $E_2$, with a single energy source, $E_0$. This is achieved by employing two asymmetric detector collimators. One detector collimator collects photons scattered through an angle $\theta_1$, while the other collects photons scattered through an angle $\theta_2$.

The collimated x-ray source generates incident photons having intensity $I_0$ and energy $E_0$. The collimated x-ray source produces a beam of incident photons which arrive at the material of interest at point P, after travelling a length $l_0$, along ray path $\alpha$. The length $l_0$ corresponds to the distance between point P and the surface of the object along ray path $\alpha$ as shown in FIG. 1. When the incident photons reach point P, photons are scattered at angles $\theta_1$ and $\theta_2$ along ray path $\beta_1$ and $\beta_2$, respectively.

Figure 2:
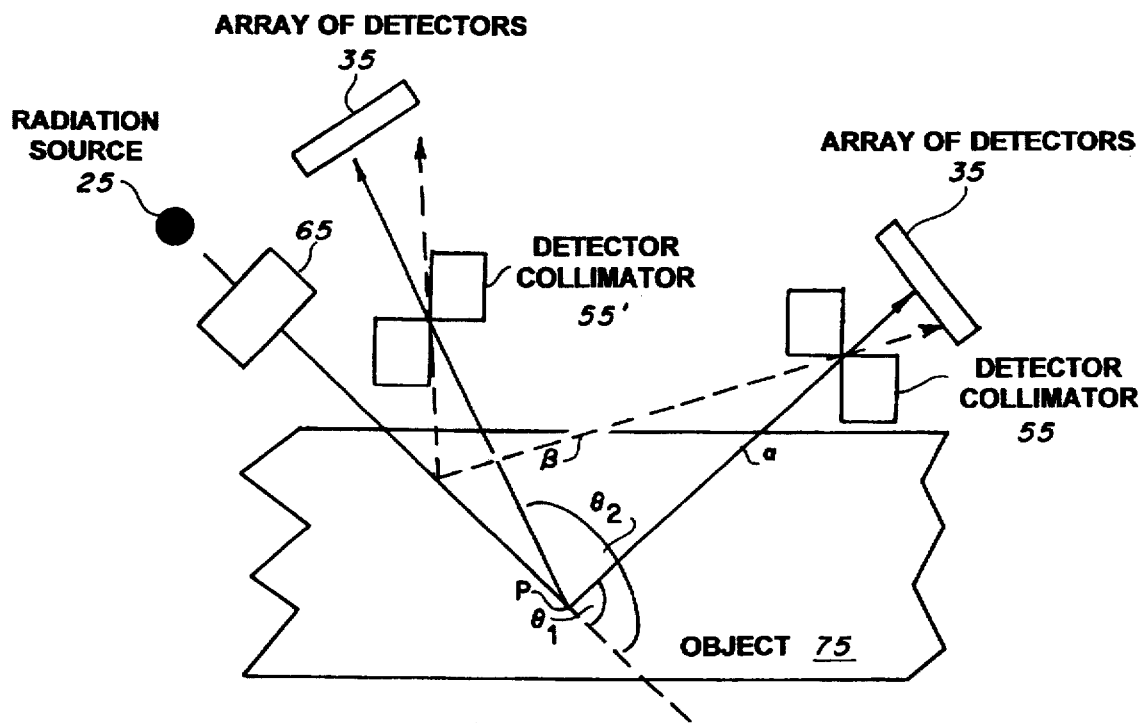
FIG. 2 illustrates the x-ray backscatter tomography (XBT) system of FIG. 1 utilizing slanted incident beams rather than vertical beams according to another embodiment of the present invention.

The photons scattered through angle $\theta_1$ are collected by a first detector collimator. These photons travel a length $l_1$ along ray path $\beta_1$, and have an energy $E_1$, and an intensity $I_1$. Length $l_1$ corresponds to the distance between point P and the surface of the object along ray path $\beta_1$ as shown in FIG. 1. The photons scattered through angle $\theta_2$ are collected by a second detector collimator. These photons travel a length $l_2$, along ray path $\beta_2$, and have an energy $E_2$, and an intensity $I_2$. The length $l_2$ is the distance between point P and the surface of the object along ray path $\beta_2$ as shown in FIG. 1. FIG. 2 shows a similar system, but having a slanted incident beam rather than a vertical incident beam.

Thus two mathematical expressions are generated from a single measurement since the first and second detector collimators are used simultaneously. These two mathematical expressions are $$I_1(P) = C_1 \rho_e(P) e^{-\mu(E_0)l_0 - \mu(E_1)l_1} \quad (3)$$

$$I_2(P) = C_2 \rho_e(P) e^{-\mu(E_0)l_0 - \mu(E_2)l_2} \quad (4)$$

According to the present invention, each expression above is then reduced to the following two equations having two unknowns, $\rho_e$ and $\mu_a(E_0)$.

$$I_1(P) = C_1 \rho_e(P) e^{-[\mu_c(E_0) + \mu_a(E_0)]l_0 - [\mu_c(E_1) + \mu_a(E_1)]l_1} \quad (5)$$

$$I_2(P) = C_2 \rho_e(P) e^{-[\mu_c(E_0) + \mu_a(E_0)]l_0 - [\mu_c(E_2) + \mu_a(E_2)]l_2} \quad (6)$$

Then, both the density and the atomic number of the material of the object can be obtained by solving two equations associated with the two detector collimators in the preferred embodiment.

Also, according to the present invention, if the incident pencil beam scans the object in raster fashion, complete volumetric information about the object can be obtained. That is, the incident pencil beam can scan the object at a plurality of points, P, in any fashion, e.g., in a straight line or at random locations in the object to obtain complete volumetric information about the object.

In the preferred embodiment of the present invention, two sets of Compton scattered photons are collected such that their scatter angles are different. As in any data acquisition system, there are experimental errors involved. Although neither an error analysis nor the optimal scatter angle have been investigated, it is reasonable to assume that the difference in two scatter angles should be large enough such that statistically meaningful results are obtained. One way of increasing the difference in angles would be to use the slanted incident beams rather than the vertical beams, as shown in FIG. 2. Also, a real time x-ray camera could substitute for the arrays of collimated detectors.

With reference to FIG. 1, the single Compton scattered intensities corresponding to point P at each detector are as follows:

$$I_1(P) = I_0 e^{-\int \alpha \mu(E_0, l_0) dl_0} \frac{d\sigma}{d\Omega} (E_0, \theta_1) d\Omega \rho_e(P) \Delta l e^{-\int \beta_1 \mu(E_1, l_1) dl_1} \epsilon(E_1) \quad (1a)$$

$$I_2(P) = I_0 e^{-\int \alpha \mu(E_0, l_0) dl_0} \frac{d\sigma}{d\Omega} (E_0, \theta_2) d\Omega \rho_e(P) \Delta l e^{-\int \beta_2 \mu(E_2, l_2) dl_2} \epsilon(E_2) \quad (1b)$$

where $\alpha$ is the ray path in the material by incident photons; $\mu(E_0, l_0)$ is the x-ray attenuation coefficient of the material at each point $l_0$ along $\alpha$ for photons of energy $E_0$; $dl_0$ is an element of distance along $\alpha$; $d\sigma/d\Omega$ is the Compton differential cross section given in units of (cm$^2$/e$^-$-sr), governed by the Klein-Nishina formula; $d\Omega$ is the solid angle subtended by the detector and its collimator; $\Delta l$ is the element of path length at point P, where this is the dimension of voxel in practice;

$$\rho_e(P) = \rho \frac{N_A Z}{W},$$

and represents the electron density, where $\rho$ is the physical density in g/cm$^3$, $N_A$ is Avogadro's number, Z is atomic number, and W is atomic weight at point P; and $\epsilon(E_1)$ and $\epsilon(E_2)$ each are the detector efficiency at energy $E_1$ and $E_2$, respectively.

More specifically, $I_1(P)$ is the intensity of light detected by the first detector corresponding to point P, and $I_2(P)$ is the intensity of light detected by the second detector corresponding to point P as illustrated in FIG. 1. Equation (1a) therefore calculates the resultant intensity of light at angle $\theta_1$, and equation (1b) calculates the resultant intensity of light at angle $\theta_2$.

$I_0$ is a known value, i.e., this value is the intensity of light as it leaves the source collimator and is therefore set by the user of the source collimator.

The x-ray attenuation coefficient, $\mu$, varies as a function of energy, and changes as the intensity of light travels a distance, dl through the object. Accordingly, $\mu$ is integrated along the ray path being travelled, i.e., along $\alpha$, $\beta_1$, or $\beta_2$, as indicated in equations (1a) and (1b) above. The value of $\mu$ is obtained from known, tabulated reference tables as a function of energy, and therefore is a known value.

The x-ray attenuation coefficient in equation (1a) is obtained over the length of ray path $\alpha$, at energy $E_0$, and also over the length of ray path $\beta_1$, at energy $E_1$. In equation (1b) above, the x-ray attenuation coefficient is again obtained over the length of ray path $\alpha$, at energy $E_0$, and also over the length of ray path $\beta_2$, at energy $E_2$.

Energy $E_1$ and energy $E_2$ are the resultant energies at angle $\theta_1$ and $\theta_2$, respectively, and are each expressed as follows:

$$E_1(E_0,\theta_1) = \frac{E_0}{1 + \frac{E_0}{m_0 c^2}(1 - \cos\theta_1)}$$

$$E_2(E_0,\theta_2) = \frac{E_0}{1 + \frac{E_0}{m_0 c^2}(1 - \cos\theta_2)}$$

The Compton differential cross section, $d\sigma/d\Omega$, is also a known value, calculated by using the known Klein-Nishina formula, set forth below, incorporated herein by reference.

The total cross section for Compton scattering, based upon the original work of Klein-Nishina, is given by the following known expression (note that $\alpha$ here represents the energy of a given photon):

$$\sigma = 2\pi r_0^2 \left\{ \left(\frac{1+\alpha}{\alpha^2}\right)\left(\frac{2(1+\alpha)}{1+2\alpha} - \frac{\ln(1+2\alpha)}{\alpha}\right) + \frac{\ln(1+2\alpha)}{2\alpha} - \frac{1+3\alpha}{(1+2\alpha)^2}\right\}$$

where $r_0 = 2.81794 \times 10^{-13}$ cm and represents the classical radius of the electron. This cross section has been tabulated and plotted by the NBS (National Bureau of Standards).

The Klein-Nishina differential cross section for scattering of a photon of energy $\alpha$, at an angle of $\mu$, within $d\mu$ of cos $\theta$, is then given by:

$$\sigma(\alpha,\mu)d\mu = \pi r_0^2 \left(\frac{\alpha'}{\alpha}\right)^2 \left(\frac{\alpha'}{\alpha} + \frac{\alpha}{\alpha'} + \mu^2 - 1\right) d\mu.$$

The solid angle subtended by each detector and its collimator of the present invention, $d\Omega$, is the angle viewed from each detector and its collimator, and is a faculty of the geometry of each detector and its collimator and is therefore another measurable, known value.

The element of path length in the vicinity of point P, $\Delta l$, is the thickness of the voxel, in practice, i.e., the thickness of the voxel along the primary x-ray path. The voxel is a volume element defined by the intersection of the collimated x-ray beam and the field of view of a collimated detector, and has dimensions determined by the collimator geometries. The voxel thickness, $\Delta l$, can be determined by dividing the thickness of the material that is subtended by the detector array by the number of detectors in the array, and is therefore an obtainable, known value.

Equations (1a) and (1b) above can be simplified using a system parameter $C_1$, as follows:

$$I_1(P) = C_1 e^{-\int_0^{\alpha} \mu(E_0,l_0) dl_0} \rho_e(P) e^{-\int_{\beta_1} \mu(E_1,l_1) dl_1} \tag{2a}$$

$$I_2(P) = C_1 e^{-\int_0^{\alpha} \mu(E_0,l_0) dl_0} \rho_e(P) e^{-\int_{\beta_2} \mu(E_2,l_2) dl_2} \tag{2b}$$

Without loss of generality, the incident x-ray is assumed to be monoenergetic for this derivation. The use of a polyenergetic x-ray source requires the integration of terms which are a function of energy over the x-ray spectrum of the source.

From equations (2a) and (2b), the photon intensities scattered at the position P with angles $\theta_1$ and $\theta_2$ (or with the same angle, $\theta_1$) are accordingly expressed as follows:

$$I_1(P) = C_1 \rho_e(P) e^{-\mu(E_0) l_0 - \mu(E_1) l_1} \tag{3}$$

$$I_2(P) = C_2 \rho_e(P) e^{-\mu(E_0) l_0 - \mu(E_2) l_2} \tag{4}$$

The photoelectric linear attenuation coefficient is the sum of scatter and absorption for photon energies less than 1.02 MeV as follows:

$$\mu(Z,E) = \mu_c(Z,E) + \mu_a(Z,E) \tag{5}$$

where $\mu_c$ can be further rewritten as $$\mu_c(E) = N\sigma_c = \frac{\rho N_A}{W} Z\sigma_{c,e} = \rho_e \sigma_{c,e}(E) \tag{6}$$

where N, and $\sigma_c(E)$, and $\sigma_{c,e}(E)$ are atom density, the Compton cross section per atom and per electron, respectively, and are values obtainable from known tabulated sources.

The photoelectric absorption coefficient is expressed as $$\mu_a(Z,E) = N\sigma_a(Z,E) = CNZ^m E^n \tag{7}$$

where C, m, and n are constants, obtained numerically.

As discussed earlier, the expression for the energy of the scattered photon in terms of the photon scattering angle $\theta$ is $$E'(E,\theta) = \frac{E_0}{1 + \frac{E_0}{m_0 c^2}(1 - \cos\theta)} \tag{8}$$

where $E_0$ is the energy of the incident photon, E' is the energy of the scattered photon at a particular angle, and $m_0 c^2$ is the rest mass energy of an electron (511 KeV).

At a given scatter angle, the above equation is simplified to, $$E' = C'_3 E_0 \tag{9}$$

Then at a given material with Z, $$\mu_a(E_1) = \mu_a(C'_3 E_0) = C_3 \mu_a(E_0) \tag{10}$$

Similarly, $$\mu_a(E_2) = \mu_a(C'_4 E_0) = C_4 \mu_a(E_0) \tag{11}$$

In above equations, $C'_3$, $C_3$, $C'_4$, and $C_4$ are constants, obtained numerically.

Substituting equation (5) into equations (3) and (4) gives the following equations:

$$I_1(P) = C_1 \rho_e(P) e^{-[\mu_c(E_0) + \mu_a(E_0)]l_0 - [\mu_c(E_1) + \mu_a(E_1)]l_1} \quad (12)$$

$$I_2(P) = C_2 \rho_e(P) e^{-[\mu_c(E_0) + \mu_a(E_0)]l_0 - [\mu_c(E_2) + \mu_a(E_2)]l_2} \quad (13)$$

Substituting equations (6), (10) and (11) into equations (12) and (13) gives $$I_1(P) = C_1 \rho_e(P) e^{-[\rho_e \sigma_{c,e}(E_0) + \mu_a(E_0)]l_0 - [\rho_e \sigma_{c,e}(E_1) + C_3 \mu_a(E_0)]l_1} \quad (14)$$

$$I_2(P) = C_2 \rho_e(P) e^{-[\rho_e \sigma_{c,e}(E_0) + \mu_a(E_0)]l_0 - [\rho_e \sigma_{c,e}(E_2) + C_4 \mu_a(E_0)]l_2} \quad (15)$$

The values of $C_1$, $C_2$, $C_3$, $C_4$, $l_0$, $l_1$, $l_2$, $\sigma_{c,e}(E_0)$, $\sigma_{c,e}(E_1)$, $\sigma_{c,e}(E_2)$ can be acquired by calculation, by measurement, and by referral to known scientific data tables, as discussed earlier, thus leaving two unknowns, $\rho_e$ and $\mu_a$ ($E_0$), in equations (14) and (15).

When solved, $$\rho_e = \frac{\left[ (l_0 + C_4 l_2) \ln \frac{C_1 \rho_e}{I_1} - (l_0 + C_3 l_1) \ln \frac{C_2 \rho_e}{I_2} \right]}{a - b} \quad (16)$$

where $b = (l_0 + C_3 l_1)[\sigma_{c,e}(E_0) l_0 + \sigma_{c,e}(E_2) l_2]$ and
$a = (l_0 + C_4 l_2)[\sigma_{c,e}(E_0) l_0 + \sigma_{c,e}(E_1) l_1]$.

This is a transcendental equation which can be solved for $\rho_e$ numerically. Subsequently, $\mu_a(E_0)$ and Z are easily obtained using equations (14), (15) and (7).

As shown above, by using the method and apparatus of the present invention, two expressions can be obtained which can be mathematically reduced to two equations having only two unknowns. Thus, both the density and the atomic number of a material of an object can be obtained by solving the two equations having the two unknowns.

Although preferred embodiments of the invention have been shown and described, it will be appreciated by those skilled in the art that changes may be made in these embodiments without departing from the principles and spirit of the invention, the scope of which is defined in the claims and their equivalents.

I claim:

1. A method for determining both density and atomic number of a material of an object using Compton scattering, said method simultaneously employing at least two detector/collimators for detecting photons having been Compton scattered, said first detector/collimator collecting photons scattered through angle $\theta_1$, and said second detector/collimator collecting photons scattered through $\theta_2$, said method further employing a means for obtaining two expressions associated with said first and second detector/collimators wherein said expressions are solved to determine both the density and atomic number of the material of an object.

2. A method for determining the material composition of the material of an object by using Compton scattering comprising:

(a) simultaneously employing first and second detector/collimators to collect photons scattered through angles $\theta_1$ and $\theta_2$.

(b) obtaining two expressions associated with said first and second detector/collimators and reducing said two expressions to two equations having two unknowns, $\rho_e$ and $\mu_a(E_0)$, (c) determining the density and atomic number of said material of said object.

3. The method according to claim 2 wherein the step of obtaining two expressions associated with said first and second detector/collimators comprises evaluation of the following equations:

$$I_1(P) = I_0 e^{-\int_\alpha \mu(E_0, l_0) dl_0} \frac{d\sigma}{d\Omega}(E_0, \theta_1) d\Omega \rho_e(P) \Delta l e^{-\int_{\beta_1} \mu(E_1, l_1) dl_1} \epsilon(E_1) \quad (1a)$$

$$I_2(P) = I_0 e^{-\int_\alpha \mu(E_0, l_0) dl_0} \frac{d\sigma}{d\Omega}(E_0, \theta_2) d\Omega \rho_e(P) \Delta l e^{-\int_{\beta_2} \mu(E_2, l_2) dl_2} \epsilon(E_2) \quad (1b)$$

wherein equations (1a) and (1b) each represent scattered intensities corresponding to point P, wherein point P is the point at which said object is irradiated with a beam of incident photons, wherein $\alpha$ is the ray path in the material by incident photons, $\mu(E_0, l_0)$ is the x-ray attenuation coefficient of the material at each point $l_0$ along $\alpha$ for photons of energy $E_0$, $dl_0$ is an element of distance along $\alpha$, $d\sigma/d\Omega$ is the Compton differential cross section given in units of (cm$^2$/e$^-$-sr) governed by the Klein-Nishina formula, $d\Omega$ is the solid angle subtended by the detector and its collimator, $\Delta l$ is the element of path length at point P, where this is the dimension of voxel in practice, $$\rho_e(P) = \rho \frac{N_A Z}{W}$$

and represents the electron density, where $\rho$ is the physical density in g/cm$^3$, $N_A$ is Avogadro's number, Z is atomic number, and W is atomic weight at point P, and $\epsilon(E_1)$ and $\epsilon(E_2)$ are each the detector efficiency at energy $E_1$ and $E_2$, respectively; wherein equations (1a) and (1b) are rewritten using a system parameter $C_1$ as follows:

$$I_1(P) = C_1 e^{-\int_\alpha \mu(E_0, l_0) dl_0} \rho_e(P) e^{-\int_{\beta_1} \mu(E_1, l_1) dl_1} \quad (2a)$$

$$I_2(P) = C_1 e^{-\int_\alpha \mu(E_0, l_0) dl_0} \rho_e(P) e^{-\int_{\beta_2} \mu(E_2, l_2) dl_2} \quad (2b)$$

wherein said two expressions associated with said first and second detector/collimators are:

$$I_1(P) = C_1 \rho_e(P) e^{-\mu(E_0) l_0 - \mu(E_1) l_1} \quad (3)$$

$$I_2(P) = C_2 \rho_e(P) e^{-\mu(E_0) l_0 - \mu(E_2) l_2} \quad (4)$$

wherein equation (3) is the photo intensity of the scattered photons detected by said first detector/collimators at said angle $\theta_1$, and equation (4) is the photo intensity of the scattered photons detected by said second detector/collimators at said angle $\theta_2$.

4. The method according to claim 3 wherein said reducing of said two expressions associated with said first and second detector/collimators comprises evaluation of the following equations:

$$\mu(Z, E) = \mu_c(Z, E) + \mu_a(Z, E) \quad (5)$$

wherein $\mu$ is the total linear attenuation coefficient and is the sum of scatter and absorption for photon energies less than 1.02 MeV, $\mu_c$ is the linear scatter coefficient, and $\mu_a$ is the linear absorption coefficient;

wherein $\mu_c$ can be rewritten as follows:

$$\mu_c(E) = N\sigma_c = \frac{\rho N_A}{W} Z\sigma_{c,e} = \rho_e \sigma_{c,e}(E) \qquad (6)$$

where $N$, $\sigma_c(E)$, and $\sigma_{c,e}(E)$ are atom density, the Compton cross section per atom and per electron, respectively, and substitution of equation (5) into equations (3) and (4) results in the following equations:

$$I_1(P) = C_1 \rho_e(P) e^{-[\mu_c(E_0) + \mu_a(E_0)]l_0 - [\mu_c(E_1) + \mu_a(E_1)]l_1} \qquad (7)$$

$$I_2(P) = C_2 \rho_e(P) e^{-[\mu_c(E_0) + \mu_a(E_0)]l_0 - [\mu_c(E_2) + \mu_a(E_2)]l_2} \qquad (8).$$

5. The method according to claim 4 wherein said reducing of said two expressions associated with said first and second detector/collimators further comprises evaluation of the following equations:

$$E_1(E_0, \theta_1) = \frac{E_0}{1 + \frac{E_0}{m_0 c^2}(1 - \cos\theta_1)} \qquad (9a)$$

$$E_2(E_0, \theta_2) = \frac{E_0}{1 + \frac{E_0}{m_0 c^2}(1 - \cos\theta_2)} \qquad (9b)$$

wherein equations (9a) and (9b) are expressions for the energy of the scattered photon in terms of photo scattering angle $\theta_1$ and $\theta_2$, respectively;

wherein $E_0$ is the energy of the incident photon, $E_1$ and $E_2$ are the energies of the scattered photon at angle $\theta_1$ and $\theta_2$, respectively, and $m_0 c^2$ is the rest mass energy of an electron (511 KeV);

wherein, at a given scatter angle, equations (9a) and (9b) are simplified to:

$$E_1 = C'_3 E_0 \qquad (10a)$$

$$E_2 = C'_4 E_0 \qquad (10b).$$

6. The method according to claim 5 wherein said reducing of said two expressions associated with said first and second detector/collimators further comprises evaluation of the following equations:

$$\mu_a(Z, E) = N\sigma_a(Z, E) = CNZ^m E^n \qquad (11)$$

wherein $\mu_a$ is the linear absorption coefficient; and substituting equations (10a) and (10b) into equation (11) gives, at a given material $Z$, the following equations (12) and (13):

$$\mu_a(E_1) = \mu_a(C'_3 E_0) = C_3 \mu_a(E_0) \qquad (12)$$

and $$\mu_a(E_2) = \mu_a(C'_4 E_0) = C_4 \mu_a(E_0) \qquad (13)$$

wherein $C'_3$, $C_3$, $C'_4$ and $C_4$ are constants.

7. The method according to claim 6 wherein said reducing said two expressions associated with said first and second detector/collimators further comprises substitution of equations (6), (12) and (13) into equations (7) and (8) to give the following two equations (14) and (15) having two unknowns, $\rho_e$ and $\mu_a(E_0)$:

$$I_1(P) = C_1 \rho_e(P) e^{-[\rho_e \sigma_{c,e}(E_0) + \mu_a(E_0)]l_0 - [\rho_e \sigma_{c,e}(E_1) + C_3 \mu_a(E_0)]l_1} \qquad (14)$$

$$I_2(P) = C_2 \rho_e(P) e^{-[\rho_e \sigma_{c,e}(E_0) + \mu_a(E_0)]l_0 - [\rho_e \sigma_{c,e}(E_2) + C_4 \mu_a(E_0)]l_2} \qquad (15).$$

8. The method according to claim 7, wherein the step of determining the density and atomic number of said material of said object comprises evaluating equations (14) and (15) wherein $\rho_e$ is solved as follows:

$$\rho_e = \frac{\left[(l_0 + C_4 l_2)\ln\frac{C_1 \rho_e}{I_1} - (l_0 + C_3 l_1)\ln\frac{C_2 \rho_e}{I_2}\right]}{a - b} \qquad (16)$$

where $b = (l_0 + C_3 l_1)[\sigma_{c,e}(E_0)l_0 + \sigma_{c,e}(E_2)l_2]$ $a = (l_0 + C_4 l_2)[\sigma_{c,e}(E_0)l_0 + \sigma_{c,e}(E_1)l_1]$ and wherein $\mu_a(E_0)$ and $Z$ are then solved using equations (14), (15), and (11).

9. An apparatus for determining both density and atomic number of the material of an object using Compton scattering, said apparatus comprising a first detector/collimator and a second detector/collimator, said first detector/collimator collecting photons scattered through angle $\theta_1$, and said second detector/collimator collecting photons scattered through $\theta_2$, said apparatus further comprising a means for obtaining two expressions associated with said first and second detector/collimators wherein said expressions are solved to determine both the density and atomic number of the material of an object.

10. An apparatus for determining the material composition of the material of an object using Compton scattering comprising:

(a) first and second detector/collimators for collecting photons scattered through angles $\theta_1$ and $\theta_2$, (b) means for obtaining two expressions associated with said first and second detector/collimators and reducing said two expressions associated with said first and second detector/collimators to two equations having two unknowns, $\rho_e$ and $\mu_a(E_0)$, (c) means for determining the density and atomic number of the material of said object.

11. The apparatus according to claim 10, wherein said means for obtaining two expressions comprises evaluating the following equations:

$$I_1(P) = I_0 e^{-\int_\alpha \mu(E_0, l_0) dl_0} \frac{d\sigma}{d\Omega}(E_0, \theta_1) d\Omega \rho_e(P) \Delta l e^{-\int_{\beta_1} \mu(E_1, l_1) dl_1} \epsilon(E_1) \qquad (1a)$$

$$I_2(P) = I_0 e^{-\int_\alpha \mu(E_0, l_0) dl_0} \frac{d\sigma}{d\Omega}(E_0, \theta_2) d\Omega \rho_e(P) \Delta l e^{-\int_{\beta_2} \mu(E_2, l_2) dl_2} \epsilon(E_2) \qquad (1b)$$

wherein equations (1a) and (1b) represent scattered intensities corresponding to point P, wherein point P is the point at which said object is irradiated with a beam of incident photons, wherein:

α is the ray path in the material by incident photons, $\mu(E_0, l_0)$ is the x-ray attenuation coefficient of the material at each point $l_0$ along α for photons of energy $E_0$.

$dl_0$ is an element of distance along α.

$d\sigma/d\Omega$ is the Compton differential cross section given in units of (cm²/e⁻−sr) governed by the Klein-Nishina formula.

$d\Omega$ is the solid angle subtended by the detector and its collimator.

$\Delta l$ is the element of path length at point P, where this is the dimension of voxel in practice.

$$\rho_e(P) = \rho \frac{NZ}{W}$$

and represents the electron density, where ρ is the physical density in g/cm3, $N_A$ is Avogadro's number, Z is atomic number, W is atomic weight at point P, and $\epsilon(E_1)$ and $\epsilon(E_2)$ are each the detector efficiency at energy $E_1$ and $E_2$, respectively;

wherein equations (1a) and (1b) are rewritten using a system parameter $C_1$ as follows:

$$I_1(P) = C_1 e^{-\int_\alpha \mu(E_0, l_0)dl_0} \rho_e(P) e^{-\int_{\beta_1} \mu(E_1, l_1)dl_1} \quad (2a)$$

$$I_2(P) = C_1 e^{-\int_\alpha \mu(E_0, l_0)dl_0} \rho_e(P) e^{-\int_{\beta_2} \mu(E_2, l_2)dl_2} \quad (2b)$$

wherein said two expressions with said first and second detector/collimators are $$I_1(P) = C_1 \rho_e(P) e^{-\mu(E_0)l_0 - \mu(E_1)l_1} \quad (3)$$

$$I_2(P) = C_2 \rho_e(P) e^{-\mu(E_0)l_0 - \mu(E_2)l_2} \quad (4)$$

wherein equation (3) is the photo intensity of the scattered photons detected by said first detector/collimators at said angle $\theta_1$, and equation (4) is the photo intensity of the scattered photons detected by said second detector/ collimators of said angle $\theta_2$.

12. The apparatus according to claim 11 wherein said means for reducing said two expressions associated with said first and second detector/collimators comprises means for evaluating the following equations:

$$\mu(Z,E) = \mu_c(Z,E) + \mu_a(Z,E) \quad (5)$$

wherein μ is the total linear attenuation coefficient, and is the sum of scatter and absorption for photon energies less than 1.02 MeV;

wherein $\mu_c$ is the linear scatter coefficient, and $\mu_a$ is the linear absorption coefficient;

wherein $\mu_c$ can be rewritten as follows:

$$\mu_c(E) = N\sigma_c = \frac{\rho N_A Z}{W} \sigma_{c,e} = \rho_e \sigma_{c,e}(E) \quad (6)$$

where N, $\sigma_c(E)$, and $\sigma_{c,e}(E)$ are atom density, the Compton cross section per atom and per electron, respectively, and substitution of equation (5) into equations (3) and (4) results in the following formulas:

$$I_1(P) = C_1 \rho_e(P) e^{-[\mu_c(E_0) + \mu_a(E_0)]l_0 - [\mu_c(E_1) + \mu_a(E_1)]l_1} \quad (7)$$

$$I_2(P) = C_2 \rho_e(P) e^{-[\mu_c(E_0) + \mu_a(E_0)]l_0 - [\mu_c(E_2) + \mu_a(E_2)]l_2} \quad (8)$$

13. The apparatus according to claim 12 wherein said means reducing said two expressions associated with said first and second detector/collimators further comprises means for evaluating the following equations:

$$E_1(E_0, \theta_1) = \frac{E_0}{1 + \frac{E_0}{m_0 c^2}(1 - \cos\theta_1)} \quad (9a)$$

$$E_2(E_0, \theta_2) = \frac{E_0}{1 + \frac{E_0}{m_0 c^2}(1 - \cos\theta_2)} \quad (9b)$$

wherein equations (9a) and (9b) are expressions for the energy of the scattered photon in terms of photo scattering angle $\theta_1$ and $\theta_2$, respectively, wherein $E_0$ is the energy of the incident photon, $E_1$ and $E_2$ are the energies of the scattered photon at angle $\theta_1$ and $\theta_2$, respectively, and $m_0 c^2$ is the rest mass energy of an electron (511 KeV);

wherein, at a given scatter angle, equations (9a) and (9b) are simplified to:

$$E_1 = C'_3 E_0 \quad (10a)$$

$$E_2 = C'_4 E_0 \quad (10b)$$

14. The apparatus according to claim 13 wherein said means for reducing said two expressions associated with said first and second detector/collimators further comprises means for evaluating the following equations:

$$\mu_a(Z,E) = N\sigma_a(Z,E) = CNZ^n E^m \quad (11)$$

wherein $\mu_a$ is the linear absorption coefficient and substituting equations (10a) and (10b) into equation (11) gives, at a given material Z, the following equations (12) and (13):

$$\mu_a(E_1) = \mu_a(C'_3 E_0) = C_3 \mu_a(E_0) \quad (12)$$

and $$\mu_a(E_2) = \mu_a(C'_4 E_0) = C_4 \mu_a(E_0) \quad (13)$$

wherein $C'_3$, $C_3$, $C'_4$ and $C_4$ are constants.

15. The apparatus according to claim 14, wherein said means for reducing said two expressions associated with said first and second detector/collimators further comprises substitution of equations (6), (12) and (13) into equations (7) and (8) to give the following expressions (14) and (15) having two unknowns, $\rho_e$ and $\mu_a(E_0)$:

$$I_1(P) = C_1 \rho_e(P) e^{-[\rho_e \sigma_{c,e}(E_0) + \mu_a(E_0)]l_0 - [\rho_e \sigma_{c,e}(E_1) + C_3 \mu_a(E_0)]l_1} \quad (14)$$

$$I_2(P) = C_2 \rho_e(P) e^{-[\rho_e \sigma_{c,e}(E_0) + \mu_a(E_0)]l_0 - [\rho_e \sigma_{c,e}(E_2) + C_4 \mu_a(E_0)]l_2} \quad (15)$$

16. The apparatus according to claim 15, wherein said means for determining the density and atomic number of said material of said object comprises evaluating equations (14) and (15), wherein $\rho_e$ is solved as follows:

$$\rho_e = \frac{\left[(l_0 + C_4 l_2)\ln\frac{C_1 \rho_e}{I_1} - (l_0 + C_3 l_1)\ln\frac{C_2 \rho_e}{I_2}\right]}{a - b} \quad (16)$$

where $b = (l_0 + C_3 l_1)[\sigma_{c,e}(E_0)l_0 + \sigma_{c,e}(E_2)l_2]$ $a = (l_0 + C_4 l_2)[\sigma_{c,e}(E_0)l_0 + \sigma_{c,e}(E_1)l_1]$ wherein $\mu_a(E_0)$ and Z are then solved using equations (14), (15), and (11).

17. A method for determining the material composition of the material of an object by using Compton scattering comprising:

(a) providing a radiation source;

(b) providing first and second detector/collimators;

(c) positioning said radiation source at a location exterior to one side of said object, and irradiating said object at a point P with a beam of incident photons travelling a length $l_0$, along a ray path $\alpha$ between point P and the surface of said object, having intensity $I_0$, and energy $E_0$;

(d) simultaneously employing said first detector/collimators and said second detector/collimators wherein said first detector/collimators collects photons scattered through an angle $\theta_1$, having an intensity $I_1$, and an energy $E_1$, and travelling a length $l_1$, along ray path $\beta_1$, between said point P and the surface of said object along said ray path $\beta_1$, and wherein said second detector/collimators collects photons scattered through an angle $\theta_2$, having an intensity $I_2$, and an energy $E_2$, and travelling a length $l_2$; along ray path $\beta_2$, between said point P and the surface of said object along said ray path $\beta_2$;

(e) obtaining two expressions associated with said first and second detector/collimators and reducing said two expressions to two equations having two unknowns, $\rho_e$ and $\mu_a(E_0)$;

(f) determining the density and atomic number of said material of said object.

18. An apparatus for determining the material composition of the material of an object by using Compton scattering comprising:

a radiation source positioned at a location exterior to one side of said object to irradiate said object;

a first detector/collimators for detecting photons having been Compton scattered through an angle $\theta_1$, at a known first detector/collimators position located exterior to one side of said object;

a second detector/collimators for detecting photons having been Compton scattered through an angle $\theta_2$ at a known, second detector/collimators position, different from said first detector/collimators position, located exterior to one side of said object;

means for obtaining two expressions associated with said first and second detector/collimators and reducing said two expressions associated with said first and second detector/collimators to two equations having two unknowns, $\rho_e$ and $\mu_a(E_0)$;

means for determining the density and atomic number of the material of said object.

* * * * *